United States Patent
Fox et al.

(10) Patent No.: US 12,290,927 B2
(45) Date of Patent: May 6, 2025

(54) INTERACTION CONTROLLING ROBOT

(71) Applicant: XTEND AI Inc., Middleburg, FL (US)

(72) Inventors: Harry Fox, Jerusalem (IL); David Azoulay, Jerusalem (IL); Boris Zlotnikov, Tel Aviv (IL); Andrew C. Gorelick, Ashkelon (IL); Efraim Spiro, Jerusalem (IL)

( * ) Notice: Subject to any disclaimer, the term of this patent is extended or adjusted under 35 U.S.C. 154(b) by 0 days.

(21) Appl. No.: 18/804,948

(22) Filed: Aug. 14, 2024

(65) Prior Publication Data

US 2025/0058463 A1    Feb. 20, 2025

Related U.S. Application Data

(60) Provisional application No. 63/538,142, filed on Sep. 13, 2023, provisional application No. 63/533,160, filed on Aug. 17, 2023.

(51) Int. Cl.
    B25J 9/16    (2006.01)

(52) U.S. Cl.
    CPC .......... B25J 9/163 (2013.01); B25J 9/1689 (2013.01)

(58) Field of Classification Search
    CPC ........ B25J 9/163; B25J 9/1689; B25J 9/0003; B25J 9/1628; B25J 9/1653; B25J 9/1669; B25J 11/0005; B25J 11/0045; B25J 11/009
    See application file for complete search history.

(56) References Cited

U.S. PATENT DOCUMENTS

| | | | |
|---|---|---|---|
| 2017/0228520 A1* | 8/2017 | Kidd | G16H 20/13 |
| 2017/0239812 A1* | 8/2017 | Thapliya | G06F 16/5838 |
| 2017/0282371 A1* | 10/2017 | Erhart | G06Q 30/016 |
| 2019/0179810 A1 | 6/2019 | Miller et al. | |
| 2019/0291277 A1* | 9/2019 | Oleynik | B25J 9/1669 |
| 2020/0042865 A1 | 2/2020 | Lee et al. | |
| 2020/0092465 A1 | 3/2020 | Lee et al. | |
| 2021/0170585 A1* | 6/2021 | Kim | G06N 20/00 |
| 2021/0354305 A1* | 11/2021 | Kim | B25J 13/003 |
| 2022/0266161 A1* | 8/2022 | Kawauchi | A63H 30/04 |
| 2022/0269380 A1* | 8/2022 | Tertzakian | G06F 16/248 |
| 2022/0299982 A1 | 9/2022 | Stump et al. | |
| 2023/0173683 A1* | 6/2023 | Gomez | G06F 3/017 700/246 |
| 2023/0234221 A1* | 7/2023 | Ryu | B25J 9/163 |
| 2024/0041252 A1* | 2/2024 | Wragg | A47J 36/32 |
| 2024/0217111 A1* | 7/2024 | Kuk | B25J 11/0005 |

* cited by examiner

*Primary Examiner* — Abby Y Lin
*Assistant Examiner* — Esvinder Singh
(74) *Attorney, Agent, or Firm* — JMB DAVIS BEN-DAVID

(57) ABSTRACT

A system, including an analysis server computer, a robot that is configured to participate in interactions with one or more participants; wherein the robot is configured to collect information related to the participants during the interaction, wherein the robot accepts a summary report related to the interaction from a participant or forms a summary report, wherein the robot is configured to forward the summary report to the analysis server for analysis, wherein the analysis server is configured to analyze the summary report and determine if the summary report should pass or fail, when the summary report passes the analysis server is configured to store the summary report in a database; and when the summary report fails the analysis server is configured to provide feedback to the robot with a list of problems for correction in the summary report.

21 Claims, 2 Drawing Sheets

INTERACTION CONTROLLING ROBOT

CROSS REFERENCE TO RELATED APPLICATIONS

Applicant claims priority and the benefit of U.S. provisional applications 63/533,160 and 63/538,142, filed respectively 17 Aug. and Sep. 13, 2023, the disclosures of which are incorporated herein by reference.

FIELD OF THE INVENTION

The present invention relates to robots and to robots that participate in interactions.

BACKGROUND OF THE INVENTION

Robots in the modern day fall generally into two categories. The first is an unintelligent robot with hyper-specific functionality, usually on assembly lines. The second is an intelligent, general function, sometimes mobile, robot that may use intelligence derived from both artificial intelligence (such as Cloud Artificial Intelligence) or from the processing of operational algorithms such as facial and object recognition, audio recognition etc.

Intelligent robots are becoming more and more part of everyday life. Such robots are used (for example) for medical care support, as waiters in restaurant, for takeaway deliveries and other tasks.

The intelligent robots are typically controlled by a server which stores their data and functionality. The processing power needed to operate such robots typically requires large and costly processors and peripherals. In order to be controlled by the server and have access to data, resources and services, the robot is required to have some form of communication means with the server such as Bluetooth, Wi-Fi, Zigbee etc.

When an intelligent robot interacts with a group of participants the server can help the robot to respond and act during the meeting. Additionally, it would be helpful for the robot to initiate interactions with the participants to lead the interaction to a useful result.

Accordingly, there is a need in the industry and field for a system that can efficiently and effectively control interactions between a robot and participants and check the results of such interactions.

SUMMARY OF THE INVENTION

To achieve these and other objectives, the herein system and method can efficiently and effectively assist a robot to participate in interactions with participants and check the results of the interaction.

Therefore, to achieve these and other objects, the herein disclosed invention in embodiments is directed to a system including an analysis server computer; a robot participating in interactions with one or more participants; wherein the robot collects information related to the participants during a current interaction; wherein the robot accepts a summary report related to the current interaction from a participant or generates the summary report; wherein the robot transmits said summary report to the analysis server for analysis; wherein the analysis server analyzes the summary report and determines if the summary report should pass or fail; and, wherein, when the summary report passes, the analysis server stores the summary report in a database; and, when the summary report fails, the analysis server generates feedback to the robot with a list of problems for correction in the summary report.

An aspect of an embodiment of the invention, relates to a system for participating and controlling interactions between a robot and one or more participants in the interaction. During the interaction the robot records information of the participants, for example speech, pulse rate and facial expressions. One of the participants may be a leader participant, who leads the interaction and provides a summary report to the robot. Alternatively, the robot may create a summary report of the interaction by itself. The robot transmits the summary report to an analysis server that analyzes the report, for example using AI and decides if the report passes or fails. If the report passes, the analysis server stores the summary report in a database, for example on a data server. If the report fails the analysis server generates a list of corrections and sends the list to the robot to have the summary report updated by the leader participant or by the robot. Optionally, the stored summary report may be utilized to take actions, for example prepare a meal or provide medical treatment based on the stored summary report.

There is thus provided by an embodiment of the invention, a system including:

An analysis server computer;

A robot participating in interactions with one or more participants; wherein the robot collects information related to the participants during a current interaction;

Wherein the robot accepts a summary report related to the interaction from a participant or generates the summary report;

Wherein the robot transmits the summary report to the analysis server for analysis;

Wherein the analysis server analyzes the summary report and determine if the summary report should pass or fail;

When the summary report is determined to pass by the analysis server, the analysis server stores the summary report in a database; and when the summary report is determined to fail, the analysis server generates feedback to the robot with a list of problems for correction in the summary report.

In an embodiment of the invention, the analysis server analyzes the summary report with a trained artificial intelligence (AI) model. Optionally, the analysis server analyzes the summary report considering information collected by the robot from participants of the interaction. In an embodiment of the invention, the analysis server analyzes the summary report considering information stored in the database relating to participants of the interaction. Optionally, the analysis server analyzes the summary report considering publicly available knowledge. Alternatively or additionally, the analysis server analyzes the summary report considering general medical knowledge. Further alternatively or additionally, the analysis server analyzes the summary report considering general culinary knowledge.

In an embodiment of the invention, the participant that provided the summary report is a medical practitioner and the report relates to the medical status of another participant. Optionally, the summary report is used to determine a medical status of a participant. Alternatively or additionally, the summary report is used to prepare a food order of a participant. In an embodiment of the invention, the participant that provided the summary report can request to override the determination of the analysis server.

There is further provided according to an embodiment of the invention, a method, comprising:

Conducting an interaction between a robot and one or more participants;

Collecting information related to the participants by the robot during the interaction;

The robot accepting a summary report related to the interaction from a participant or generating the summary report;

Analyzing the summary report by an analysis server;

Determining if the summary report should pass or fail;

Wherein, when the summary report is determined to pass, the analysis server stores the summary report in a database for future access; and when the summary report is determined to fail, the analysis server provides feedback to the robot with a list of problems for correction in the summary report.

In an embodiment of the invention, a non-transitory computer readable storage medium comprises computer instructions that when executed by a robot with a processor and memory are configured to perform the method described above.

BRIEF DESCRIPTION OF THE DRAWINGS

The present invention will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

In the following detailed description, numerous specific details are set forth in order to provide a thorough understanding of the invention. However, it will be understood by those skilled in the art that the present invention may be practiced without some of those specific details. In other instances, well-known methods, procedures, and components have not been described in detail so as not to obscure the present invention.

In an embodiment, the invention is directed to a system including an analysis server computer; a robot participating in interactions with one or more participants; wherein the robot collects information related to the participants during a current interaction; wherein the robot accepts a summary report related to the current interaction from a participant or generates the summary report; wherein the robot transmits the summary report to the analysis server for analysis; wherein the analysis server analyzes the summary report and determines if the summary report should pass or fail; and, wherein, when the summary report is determined to pass, the analysis server stores the summary report in a database; and, when the summary report is determined to fail, the analysis server generates feedback to the robot with a list of problems for correction in the summary report.

Figure 1:
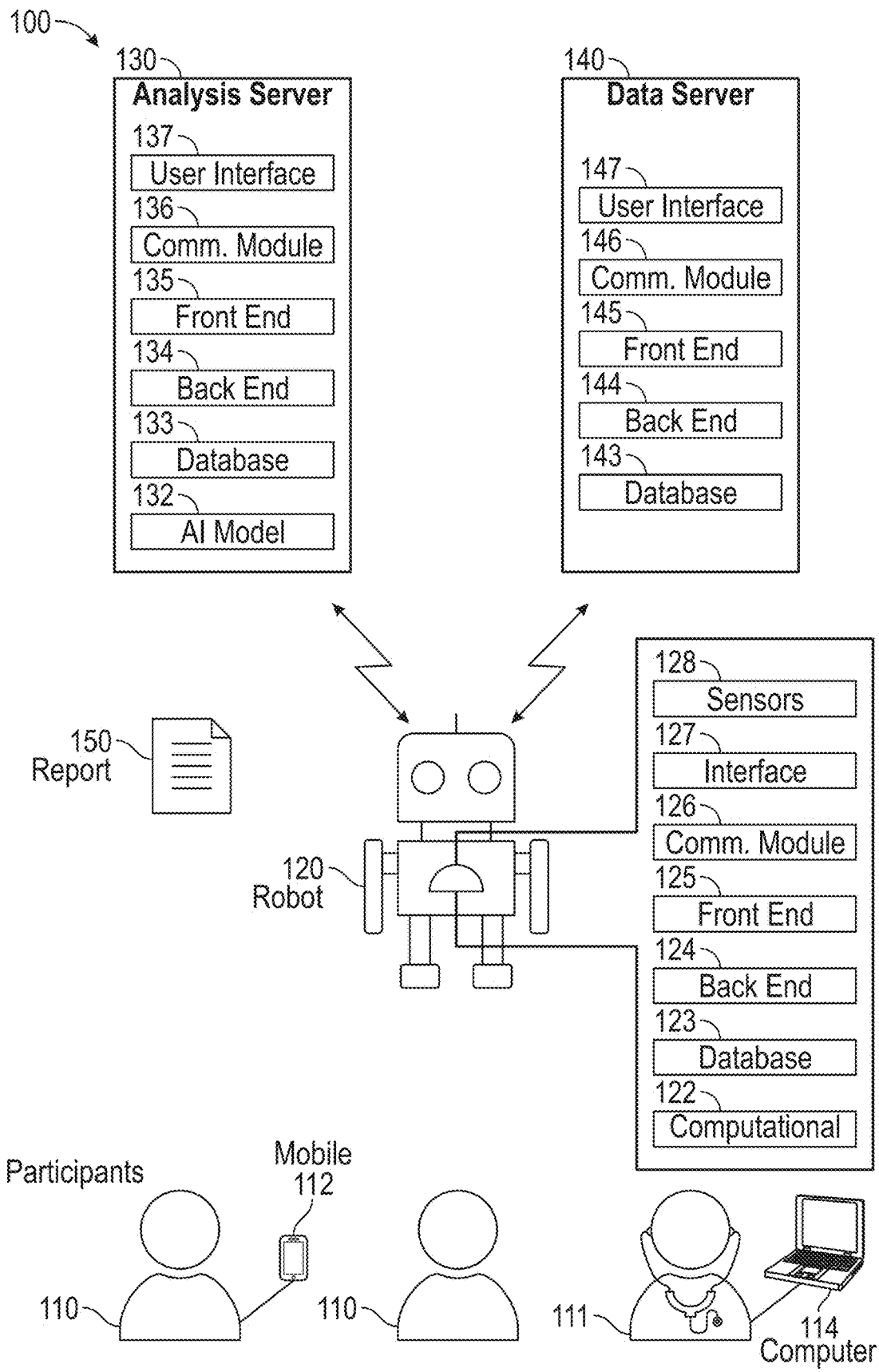
FIG. 1 is a schematic illustration of a system with an interaction controlling robot, according to an embodiment of the invention.
Figure 2:
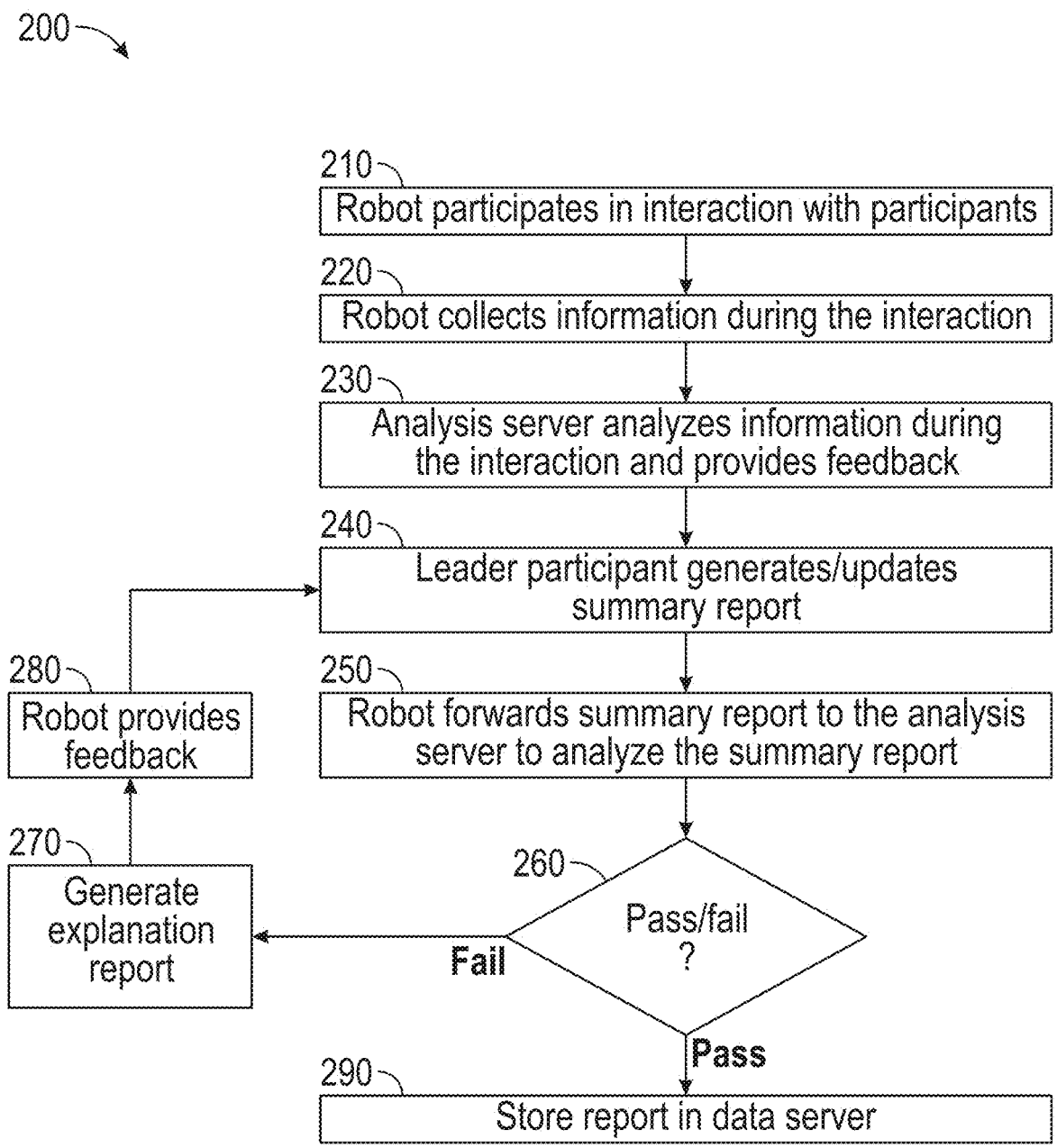
FIG. 2 is a schematic illustration of a method of controlling interactions with a robot, according to an embodiment of the invention.

FIG. 1 is a schematic illustration of a system 100 with an interaction controlling robot 120 and FIG. 2 is a schematic illustration of a method 200 of controlling interactions with a robot 120, according to an embodiment of the invention. Robot 120 is configured to interact with one or more participants 110 in an interaction and provide feedback. In an embodiment of the invention, one of the participants may lead the interaction with the robot 120, for example serving as a leader participant 111. Optionally, the leader participant 111 can be a service provider representing an organization providing a service to the other participants 110 or the leader participant 111 may be one of a group of client participants 110 interacting with robot 120, who represents the organization.

In an embodiment of the invention, with reference to FIG. 2, the robot 120 participates (210) in the interaction and optionally, collects (220) input from the participants 110. For example the robot 120 may use various sensors 128 to interact with the participants 110 or may receive information from participant devices. In an embodiment of the invention, the sensors 128 include a microphone, a camera, a magnetometer, an accelerometer, human vital sign (temperature, blood pressure, pulse, pulse oximetry, etc.) measurement sensors, and other sensors. The robot may be configured to record conversation, film the interaction, measure vital signs of the participants (e.g., heart rate, SpO2, breathing rate, pain diagrams, brain waves, pulse rate), use facial recognition to identify the participants 110 or record their presence, receive text messages or files from mobile devices of the participants (e.g., a mobile telephone 112 or computer 114), receive input through an interaction interface of the robot 120 and other options. Optionally, during the interaction the robot 120 forwards (230) some of the information to an analysis server 130 to analyze the interaction. Optionally, the analysis server 130 may use artificial intelligence or a Large Language Model (LLM) to analyze (230) the information and provide feedback to assist the robot 120 to handle the interaction.

In an embodiment of the invention, the robot 120 and/or analysis server 130 may include processes to enable: Image processing, image recognition, voice/audio recognition, voice matching, voice recording, accepting dictations, navigation, the ability to move, the ability to speak; speech to text (STT), text to speech (TTS), natural language processing (NLP), optical symbol recognition (OSR), optical character recognition (OCR), face recognition; identifying a person's vital signs (e.g., SpO2, heart rate breathing rate, pain diagrams, brain waves, pulse rate), and other functions.

In some embodiments of the invention, the robot 120 includes a user interface with a display on the robot screen/face to interact with the participants 110 and especially the leader participant 111. Optionally, the display may function as a touch screen. The robot 120 may be provided with a user interface (e.g., a GUI or graphical user interface) which is tailored to the particular application to assist users with data entry and verification. There may be provided a default or standard GUI template which a user can modify by adding, removing, or changing data fields and labels. Alternatively, the GUI may be generated by analyzing the relevant data and determining the corresponding data fields that need to be included in the GUI. In yet another alternative, a user may be provided with the ability to "build your own" GUI by adding text boxes, labels, pictures and the like directly at the robot or via an external device using Wi-Fi, Bluetooth, NFC, USB, or any appropriate interface.

Entering data via the GUI may involve retrieving appropriate data from external devices and displaying the data in the corresponding data field of the GUI. The system may be configured to map data from specific devices to specific data fields in the generated report. For example, this may involve mapping data from a smart watch to corresponding vital sign fields in a report. In certain environments involving many users, a user may be able to use a mobile app on their device (e.g., smartphone) to connect with the system. In a more controlled environment with a limited set of users, such as a medical facility, the system may be configured to connect with specific sets of users only.

Once a user device is connected, the system may be able to pull data from that device and display it in the appropriate location within the GUI. Pulling data from the user device may be triggered by user selection on the GUI to initiate external device interface and data download. Alternatively, data transfer may happen automatically, such as when a connected device is within range of the system. Alternatively, data transfer can be initiated from the user's external device. In yet another alternative, data may be entered manually by typing, touchscreen, voice input or the like.

In an embodiment of the invention, during the interaction the leader participant 111 generates (240) a summary report 150 to summarize the interaction and/or initiate a request for actions responsive to the interaction. Optionally, the summary report 150 can be a medical annotation, a prescription, a table order or other types of reports.

In an embodiment of the invention, robot 120 forwards (250) the summary report 150 to the analysis server 130 to analyze the summary report 150. If (260) the information in the report is accepted, it is tagged with a "pass" tag for passing the analysis. If (260) the information is not accepted, it is tagged with a "fail" tag for failing the analysis. Optionally, when failing is indicated, the analysis server 130 generates (270) an explanation report explaining what inconsistencies or errors were found in the information and sends the explanation report to robot 120. The robot 120 provides (280) the explanation report as feedback to the leader participant 111. In an embodiment of the invention, the leader participant 111 updates (240) the summary report 150 responsive to the comments of the analysis server 130.

In an embodiment of the invention, the robot 120 provides feedback to the leader participant 111 to correct inconsistencies or errors in the summary report 150. Optionally, the leader participant 111 updates (240) the summary report 150 and resubmits it via robot 120. In an embodiment of the invention, if the analysis server 130 accepts the summary report 150, then the summary report 150 is tagged as passing the review and forwarded to a data server 140 that stores (290) the information in a database for access by members of system 100.

In an embodiment of the invention, the analysis and corrections are based not only on the summary report 150 but also on other information collected by the robot 120 during the interaction. Alternatively or additionally, the corrections are based on previously stored information related to the client participants 110 or leader participant 111 or on common knowledge.

In an embodiment of the invention, robot 120 serves to assist a medical practitioner in dealing with a patient. Robot 120 may record the conversation, play it back to the participants or ask questions for confirmation, with or without the help of server 130. Optionally, the practitioner serves as the leader participant 111 and the patient as participant 110. The practitioner may input information (e.g., a summary report 150) directly to robot 120 via a user interface 122 of the robot 120 or indirectly via a personal computer 114, mobile telephone 112, tablet or another device that communicates with the robot 120. Optionally, robot 120 is configured to upload the report with other information recorded during the interaction (e.g., patient vital signs, or an audio file or transcription of the patient's explanations). In an embodiment of the invention, analysis server 130 analyzes the practitioner's report with information provided by the robot 120 and/or information from the patient's medical history with common knowledge to verify the integrity of the details in the practitioner's report. For example, the analysis server may invoke an Artificial Intelligence (AI) model to check for medical accuracy.

In an embodiment of the invention, analysis server 130 provides recommendations and/or corrections to the practitioner's report, for example that a specific medicine is not advisable for the patient, that the dosage should be different or that the patient should be referred to different tests or additional tests.

In an embodiment of the invention, the robot 120 receives the recommendations and forwards them to the practitioner to update the report, for example via the interface 122 or by communicating them to the practitioner's computer 114. The practitioner can then update the report or instruct the analysis server 130 to ignore the recommendations. The robot 120 is then instructed to process the updated report, for example to store the report on data server 140 in the patient's electronic health record (EHR), provide the patient with a printed report, itinerary of further required actions, provide the patient with medicine or other actions that were recommended. If the practitioner instructs to ignore the recommendation this may be indicated in the records in the EHR system. In some embodiments of the invention, all versions of the report are recorded in the EHR system or in the robot's database 123, for example the initial report from the practitioner before correction and any amended versions until passing the scrutiny of the analysis server 130.

In an alternative embodiment of the invention, robot 120 serves to receive food orders from customers/participants 110 in a restaurant. Optionally, the robot may accompany a waiter, which serves as the leader participant 111 representing the organization/restaurant. The robot 120 is present to record the transaction and pass them on for review by analysis server 130. Alternatively, the robot 120 may function independently and the customer serves as the leader participant 111, for example querying the customer via audio messages and transcribing the customer's audio responses or wherein the customer responds by selecting options from a touch display that is part of the robot interface 122.

In an embodiment of the invention, the robot 120 forwards a summary report 150 to analysis server 130 to check for errors or inconsistencies, for example that a requested item is out of stock, requested items are not combinable or only available between certain hours. Optionally, the analysis server 130 reports the problems to the robot 120, and the robot 120 checks with the waiter or the customer that made the order (e.g., leader participant 111) to correct the problems in the summary report 150. In an embodiment of the invention, analysis server 130 may suggest alternatives for the customer to select from. Optionally, when the analysis server 130 tags the summary report with a pass tag, the report is stored on data server 140. The information stored on data server 140 may serve as a customer order for the kitchen of the restaurant.

In an embodiment of the invention, system 100 includes two servers: an analysis server 130 and a data server 140. The robot 120 includes a processor 124, which interacts with the servers (130, 140). The analysis server 130 is configured to receive information (e.g., summary report 150) and perform a check for accuracy. If the check passes, the analysis server 130 sends the information to data server 140 to store the information into, for example, an EHR or similar system. If the check fails, analysis server 130 returns the information to the robot 120 to revise the information, possibly with suggested changes. Optionally, the robot 120 may correct the information or request the participant who prepared the information to review the suggested changes and correct the information. Optionally, a manager or supervisor may be informed if the summary report 150 passes or fails, for example the manager or supervisor may receive a copy of the report if it fails so that he or she may intervene if desired.

When corrections are needed, the GUI may display the corrections or the need for corrections to the user. In an embodiment, the GUI may highlight the corrections needed. For example, in a medical application, a failure identified as "Overdose" may result in the GUI highlighting the prescription field of a medical report. Alternatively, a failure associated with "Misdiagnosis" may result in highlighting of the diagnosis and symptoms section of a report.

The GUI may allow the user to select recapture or input of data or may automatically trigger a recapture of data from external sources.

In an embodiment of the invention, the participant may correct the information and resubmit via robot 120 or request to bypass the analysis server 130 and have the information stored directly at data server 140.

In an embodiment of the invention, analysis server 130 and data server 140 are general purpose computers or computer programs which manages access to a centralized resource or service in a network.

In an embodiment of the invention, analysis server 130 and data server 140 may be any remote or local processor to satisfy the purposes listed below. Examples of alternatives:
  a. Network-Attached Storage (NAS);
  b. Storage Area Network (SAN);
  c. Cloud Archiving;
  d. Workgroup Sharing;
  e. Microsoft 365;
  f. Cloud Hosted Server;
  g. File Sync and Share Applications;
  h. Windows 11.

In an embodiment of the invention, analysis server 130 is a server operated for the purposes of running an AI validation check system. The AI validation check system checks data prior to the data being sent to and stored on data server 140. For our purposes, data server 140 is a server operated for the purposes of storing electronic records for reading and writing.

Analysis server 130 and data server 140 may be a single server or a set of servers. Analysis server 130 and data server 140 may be run on the same server or set of servers so long as the data first goes through the process of an AI data validation check prior to being stored in a designated memory module. The memory module is used for electronic records in which a user may access validated information.

Optionally, analysis server 130 is a server comprising an AI that is trained to check participant data for safety and accuracy and to provide a Pass or Fail rating. If the participant data fails the AI test, the AI may generate a report detailing the reasons for the failure and possibly with suggested revisions for the data. Analysis server 130 sends the original submitted data with the report of reasons for failure and suggested changes back to the participant for review. If the data passes the AI test, analysis server 130 sends the data to data server 140 to be stored.

In an embodiment of the invention, AI model 132 is responsible for checking data, possibly adding tags, providing Pass/Fail, writing a response, and possibly suggesting alternatives in the response.

The AI model 132 can be a traditional Neural Network like a Convolutional Neural Network (CNN) or a Large Language Model (LLM) that receives data as input and produces data (here, Pass or Fail, suggestions, etc.) as an output based on prior training and fine-tuning.

The general process of training and deploying an AI is understood (e.g., Data collection, feature extraction, training a model, validation and testing, prediction, and fine-tuning). More specifically, the process of training the relevant AI functionality involves gathering data and tagging the data with relevant tags. For example, in the medical field, a medicine X may have a frequency tag of one time per day for two weeks and a dosage per weight tag of 5 mg for every 10 kg of patient body weight. A disease Y may have symptom tags A, B, and C, depending on the associated symptoms. In the case of a restaurant example implementation, menus may be scanned to search for keywords to associate with allergy tags, such as peanuts or shellfish.

The training may also involve obtaining database information and acquiring relevant, non-personal data. The database information may be tagged as personal or non-personal, and may also be tagged as shareable or non-shareable depending on applicable legal constraints (e.g., in the medical field, this may be based on HIPAA compliant or non-compliant information). Only the properly obtainable information may be utilized for training purposes. The tagging may also be implemented in such a way so as to use the same set of tags for the training data as well as for the actual use data to be obtained during use of the system. In this way, the system can easily and accurately cross-reference the different data sets and input data.

The tagged data may be used to train the system to determine pass or fail based on the input data. Additionally, when a fail is indicated, the system may be configured to provide a specific subset of tags that the GUI can interpret and display appropriately. The GUI may be provided with logic that may interpret a finite subset of tags. For example, an "Overdose" tag may result in highlighting the prescription area of a medical report. The system may be trained to use this specific set of tags when generating its results for the GUI, so that the GUI will be able to properly interpret the results.

A single AI model 132 may be trained to perform several data checks to determine the pass or fail of a summary report 150. This may be a complete set of checks or a subset of checks deemed required for a pass or fail to be determined.

Alternatively, several AI models 132 may be trained on one or more data sets. Each AI model 132 may be trained on one or more data sets that may be associated with a category of checks to determine a pass/fail for that specific data set. For example, with medical data, one data set may comprise medical interactions, and another may comprise recommended dosages based on height/age/weight. Each AI model 132 can thus function as its own independent test, validating or invalidating new data based on the AI model's specific training on the medical data. In this case, any new user data would be analyzed by multiple AI models, each designed to identify a specific type of problem. If none of them flag any problem, then the data is considered validated. If any or multiple of the AI models detect a problem, then the data is sent back to the robot/participant and any other necessary recipients.

Alternatively, a single LLM can be prompted and primed to break down medical data into key sets of information to be used to determine a pass or fail. When presented with new user data, the LLM can be prompted to check the data against some or all of those sets of information already given to the LLM prior, thus performing several tests as a single model. This may also be further broken down into multiple LLMs each with its own test or set of tests (similar to the multiple AI models mentioned above).

The required tests to be performed on new incoming data can be indicated or influenced by the tags present on that data.

Some tests may be standard to perform on any incoming data while others may only be performed if indicated as necessary by a specific tag or set of tags on the new data.

The simplest example of the demarcation of tests based on tags is medical tests performed for data with medical tags and restaurant tests performed for data with restaurant tags.

In an embodiment of the invention, the Communication Module 136 and 146 comprise a router or broker that can transfer data between analysis server 130 and data server 140 or between the robot 120 and analysis server 130 and/or data server 140. This may comprise an AWS IoT MQTT (Amazon Web Services, Internet of Things) broker or other brokers may be used as an alternative. Any means known in the art that communicates data between different servers and processors or internally within servers or processors may be used here. This may be any form of wired or wireless connection. For example, Ethernet, LAN, USB, Wi-Fi, Bluetooth, etc.

In an embodiment of the invention, analysis server 130 may pull data from data server database 143 to enable the functioning of the AI (e.g., the medical history of a patient may be needed to check the safety and accuracy of a new prescription given to that patient). Data server 140 will use the data from the reports that were provided by analysis server 130.

In an embodiment of the invention, the robot 120 is configured to submit reports and revised reports to analysis server 130. Analysis server 130 is configured to return AI-reviewed reports to the robot 120. The robot 120 may also submit reports and revised reports to data server 140. Data server 140 may share a subset of data from its database that is necessary for the user to fill out or write the report to the robot 120. (e.g., patient data may be known by the robot 120 during consultation with the practitioner (e.g., doctor, nurse etc.). Optionally, the data stored in a database 123, 133 or 143 comprises but is not limited to an electronic library of information required by the robot 120 or servers 130, 140. Analysis server 130 stores data required for the AI to validate the reports. This may include a data library and a subset of the electronic records of data server 140. In an embodiment of the invention, database 133 of analysis server 130 will store a library of medical data such as medicinal interactions, medicine side-effects and effectiveness, as well as medical history of any relevant patient, and any other data required for the AI to operate properly.

Optionally, analysis server 130 may additionally have a log or history of the transactions of the reports 150. This may be a copy of the report 150, when a report 150 was sent, who sent the report 150, when the report 150 was tagged as pass/fail and the reasons thereof, and when the report 150 was uploaded to data server 140. Alternatively, this data is hosted on data server 140 or a combination of both.

In an embodiment of the invention, database 143 of data server 140 stores electronic records comprising the validated electronic records of analysis server 130. Additionally, data sent directly from the robot 120 to data server 140 is stored in the electronic records. For example, the electronic records may be an Electronic Medical Record (ERM) or Electronic Health Record (EHR) order list or menu items.

Database 123 of robot 120 stores any needed information required, beneficial, or tangential to the leader participant 111 for the purpose of writing or filling out the summary report 150 to send to analysis server 130. This may include a subset of the electronic records stored on data server 140. An example of a subset of the information stored locally on the processor from data server 140 in a medical field application is patient data from a data server 140 EHR system.

The back-end (124, 134, 144) is where the technical processes occur. "Back-end" development refers to the development of server-side logic that powers websites and apps from behind the scenes. It includes all the code needed to build out the database, server, and application.

The front-end (125, 135, 145) is where the user interaction occurs. For analysis server 130 AI training happens here. For the robot 120 participant interaction happens here such as filing reports. For data server 140, the management of the electronic records happens here. This can be done with Electronic Records Management (ERM)—wherein "an ERM" is the field of management responsible for the efficient and systematic control of the creation, receipt, maintenance, use, and disposition of records, including the processes for capturing and maintaining evidence of and information about business activities and transactions in the form of records.

Robot 120 is an interacting computational device optionally comprising a computational module 122, processor database/memory module 123, communication module 126, interface module 127, notification system and other modules. Optionally, robot 120 is a mobile interactive kiosk, which can interact with customers. In some embodiments of the invention, the robot 120 may be stationary, for example similar to a kiosk.

The communication module 126 is described above as a means of communicating between the robot 120 and the servers (130, 140).

The Interface module 127 serves as an interface that communicates with the computational module 122. This may further include a means of converting or processing interface data to be understood by the computational model. For example, an interface of a microphone may be converted to text via speech to text (STT) prior to reaching the computational module 122. The interface module 127 may optionally comprise a notification system. If present, the notification system will be contained within the interface module 127. The notification system can be responsible for generating UX/UI notifications to the user whenever a relevant report is ready to be reviewed or at any other appropriate trigger (e.g., when the analysis server 130 tags a report as "Pass" or "Fail").

In an embodiment of the invention, the interface includes a device or array of devices through which a user can interact with the processor's interface module 127. For example, a keyboard, screen, touch screen, mouse, microphone, and camera. Optionally, the interface can enable the user to interact with the processor via image recognition, facial recognition, voice recognition or voice matching, dictation, Speech-to-Text (STT), Text-to-Speech (TTS), gesture recognition, object recognition, Optical Character Recognition (OCR), QR code reading, NFC reading, scanning, mouse clicks, and typing on a keyboard or touchscreen, etc.

In an embodiment of the invention, data to be sent from the robot 120 to the analysis server 130 is gathered using the Interface 127, for example recording a dictation during a consultation, the results of a medical examinations performed during a consultation, a doctor typing up a report). Optionally, the data includes data known by the robot, for example time, IP address, Processor ID (Computer ID, Robot ID, Company ID, Facility ID and other data).

In an embodiment of the invention, the participants in the interaction may include one or more people involved with or interacting with the robot 120 for the purposes of the summary report 150 in all of its forms, for example a doctor, waiter, client, authorized user, recognized or known user, patient, customer, etc. Optionally, different participants may have different privileges, levels of access, or place in the workflow. For example, an administrator may be able to override analysis server 130 and store data directly on data server 140. Likewise, an administrator or a high level user may be designated as a recipient of a notification, possibly in addition to the original participant that sent the summary report 150.

AI Functionality

In an embodiment of the invention, a singular AI model or a multitude of AI models working in unison may be used to achieve the check and validation process. Optionally, a single AI model or multiple AI models may be used per field or task. For example a medical trained AI model and a restaurant trained AI model may be used for different fields, respectively. The medical trained AI may specialize in medicine usage and dosage. The restaurant trained AI may specialize in food safety and allergy safety.

In the case of multiple AI models in a single field, a single data entry may be analyzed by several AIs or packages of AIs. The AI may be trained to write revisions to the summary report 150. Optionally, LLMs can be used for language interpretation and responses for reports and report revisions. Alternatively, if the AI is focused on tags/keywords an LLM may not be required, and a more traditional AI model can be used. In an embodiment of the invention, a traditional model and the LLM model can be used in unison where each functions to its specialty to complete its tasks. The AI model(s) may vary from a simple set of pre-determined checks to a true AI to achieve goals. This may depend on the complexity of the validation task at hand. The AI model may discern between tags/keywords to check the report. This may be done partially through training, manual selection (creation), and learned behaviors. A Simple AI can have pre-set types of tests that it performs.

In an embodiment of the invention pertaining to a medical interaction a check is made of new prescriptions against current medications, or other medical interactions. Optionally, the AI model will check new prescriptions against the patient status including height, weight, age, pregnancy status, etc.

In an embodiment of the invention, a more complex AI can be trained to detect a Pass or Fail based on metadata tags. The tag can act as a pre-parsing of the new data so that the AI can determine how to perform the check. Different tags may be associated with different sets of background data to check against. Optionally, an opioid prescription may require a more extensive check against more medical records than for anti-biotics. New vitals data may be checked by simply making sure the values are within an acceptable range with little to no need for checking previous medical records.

In an embodiment of the invention, for each tag the AI model may require to train the AI model with many use cases for it to learn from. A use case will contain the background data (e.g., previously stored user data and general medical data), the new data input, and if the case is a pass or fail. This can be prompted/primed with an LLM. An LLM can work particularly well for parsing dictation data. AI learning algorithms will be able to find patterns between the new data, the background data, and the pass/fail result. The resulting AI model should be able to receive a new data input, analyze this input together with the appropriate set of background data (according to the tag) and make a prediction of whether the input is a Pass or Fail. An AI model can be trained to recognize output patterns for various combinations of keywords/tags. For example, the Opioids tag plus a Renewed Prescription tag may repeatedly result in Fail. An elderly patient being prescribed a medication that can cause hypertension as a side effect may repeatedly result in a Fail. An adult-level dose of medicine prescribed to a child may result in a Fail.

Below is a list of examples and use cases of how the AI model may be trained in order for the AI to operate its checks effectively. Specific but nonlimiting examples in the medical field and the restaurant field are given.

Depending on the field the invention is implemented in, the required data fields and their format in a data report will vary. For example, a restaurant robot will typically require an order form, including selected dishes, notes or personal preferences, seat locations, and the like. In the case of medical robots, such robots will typically require medical reports, including symptoms, images, pictures, vital signs, medical tests, prescriptions, and the like. For each environment, a set of background data is determined which the AI model can use as a data library to determine the accuracy of the new input. An example of background data in the medical field is medical knowledge and patient information. An example for a restaurant is the food safety protocols, the menu, and the current stock in the kitchen. For example, if a breakfast order is made in the evening, or an order is made for something that is not in stock, the AI model will return a "Fail".

In an example for a hospital, medicine interactions, patient symptoms, allergies, current prescriptions, and medical history are taken into consideration. If there is a medical interaction between the current medicine the patient is taking and a newly prescribed medicine, or an allergy to the newly prescribed medicine, the AI model will return a "Fail". Alternatively, if a prescription does not match the symptoms (stomach medication for a headache), the AI model will return a Fail. Optionally, an AI model can be trained to analyze patient data and report a failure if any of a set of high-level rules are violated. The model would be provided with a large amount of, for example, medical data about various medications, and would be told which information it should query (ex: side-effects, risks, recommended dosages, etc.). The model can be trained to extract relevant data (tags) from a patient profile (height, weight, etc.). The model can be trained to determine which correlations between tags it should flag as a failure. Alternatively, the model can be shown several examples of use cases (patient data, new input data, any relevant tags) and their result (Pass or Fail) for it to learn on its own how to make predictions. Optionally, the AI model can be trained to write a report whenever it detects a Fail. This may require further training for the AI to state which factors caused it to make a Fail. Optionally, with an LLM a user can simply prompt the LLM to say why it thinks a case is a failure.

In an embodiment of the invention, part of the report may include a suggested alternative to the attempted prescription that avoids the cause of failure (e.g., medical interaction: doctor prescribes anti-biotic A, the patient is pregnant and antibiotic A cannot be used when pregnant, AI Report: antibiotic A is in conflict with the patient's status of pregnancy, perhaps prescribe antibiotic B (safe for pregnancy)) instead and can still be effective for the patient.

In an embodiment of the invention, the AI model may store the summary report 150 using specific tags/keywords or learned behavior. For example, patient data is uploaded to the patient file in an EHR based on a tag/keyword of the patient's name and/or ID or through AI-learned behavior. In a restaurant order data can be placed in a queue for the kitchen staff to deliver to the correct table based on the table number or name of the customer.

Tags/Keywords

In an embodiment of the invention, tags are set as metadata of the report for the purposes of categorizing the report to benefit the accuracy of the validation check of the system and process. An example of the use of tags for this benefit are retrieving the appropriate data by the AI model to check the report against, running the appropriate tests on the report by the AI model, and storing the report properly in the data server 140 electronic records in the appropriate place.

The tags may be created by human users, an AI model, or a combination of both. The tags may be based on sensors 128, devices, apparatuses, and general device/robot information, examples of which can be GPS for location tag (restaurant example of location tag: tag: table 5), modality of communication, time of day, what device/robot was used, device status, etc.

Tags can be created or customized to fit these criteria by developers, users, or knowledgeable 3rd parties.

Following are examples of possible tags:
a. Known side effects of a medication can be tags;
b. Tag for allergies, diabetes;

In a restaurant a person with a food allergy or diabetes may be tagged as a fail by the AI model if the food has the allergen or is not safe for diabetics.

In a hospital setting penicillin may come up as a fail by the AI if the patient has a penicillin allergy. The AI model may suggest an alternative beta lactam antibiotic.

c. Underage tag for serving alcohol;
d. Maintenance, safety, and security tags can be used for checking device/robot functionality automatically or by a user like a technician. Safety and security tags, for example, the level of encryption.
e. Pass/Fail may further be used as a tag;

A pass tag may be mutually exclusive with the fail tag. If a report has failed in the past and has been revised or corrected and now passes, the pass tag may knock out the fail tag; Other tags may function similarly.

f. An example of a tag for a renewal of a prescription can be different from a tag for a new prescription;
g. Tags may be used generally or specifically (e.g., medical tag or benzodiazepine tag).

The system may be trained to return tags that indicate to the GUI which data fields are the cause for failure. Depending on the faulty data fields, the GUI can offer to recapture or automatically recapture data from the appropriate devices that correspond to those data fields. For example, vital signs may be recaptured using a smartwatch, location data may be recaptured from a navigation or location system, or blurry images may be recaptured using a camera.

Tag Selection:

In an embodiment of the invention, tags can be selected manually by the user. The tags can be listed in any organizational fashion appropriate, common, or customized for the user. For example, alphabetical, by category (opioids, asthma, cholesterol OR suppositories, tablets, swallow, topical, etc.), custom: common group like a quick access bar, pre-selected (e.g., medical automatically selected). Optionally, the system 100 may have a list of frequently used tags or some that might be automatically pre-selected.

Patient data like height, weight, BMI, and age ranges may be automatically selected tags. Hierarchical tags may be used where one tag automatically includes another tag or set of tags associated with it. In an exemplary case: a tag for a burger may have an additional set of tags tied down to the tag burger, such as rare, medium, well-done and tags such as no pickles, no tomatoes, etc., Conversely, once a more specific tag is selected, any appropriate higher-level tags may also automatically be selected (if a user selects "Codeine", then the "Opioids" tag will automatically be added). Tags can be automatically selected by AI or a simple report search with keywords, or manually by a user. Tags can be a combination of both methods.

In an embodiment of the invention, the AI model first scans the report and has a list of recommended tags that the user can edit. Optionally, the times when tags are selected to be used for a report, can occur at the end of a consultation or throughout the consultation. Certain tags may only be given by the AI model and certain tags may only be given by a user. For example, pass and fail tags are given exclusively by the AI model.

Tags can be assigned by the AI model through any annotation the robot has access to, for example dictation, text, recognized words or audio cues, etc. A failure tag may automatically be given if there is a lack of necessary information.

Additional Usages of Tags:

In an embodiment of the invention, tags may be highlighted. An example of highlighting tags may be to highlight them to have a low, medium, or high priority for the tags, or generally have a known in-the-art alternative to highlight or specify a priority. Optionally, a combination of the above methods may be used.

In an embodiment of the invention, certain tags may be associated with a need to contact a different user for approval or oversight. For example Any prescription with an "Opioid" tag may automatically be sent to a supervisor for approval. Any reports that are tagged with a resident user will be automatically checked by a supervisor. If the tags on a restaurant order indicate that the order contains a specialty item or potentially risky item then a specific chef may automatically be notified. For example, pufferfish must be prepared by an expert that can properly remove the poisonous parts of the fish. Optionally, meat tartar must also be prepared by an expert.

Initialization Process for System 100:

In an embodiment of the invention, initialization of the system 100 includes the following:

Analysis server 130 setup: a user will provide data from at least one of the Electronic Records and a data library to an AI model or set of AI models to train them to perform a validation test or series of validation tests. In the case of a medical clinic, the AI model may be trained, for example, on medical data to recognize medical interactions, side effects, risks, etc. In the case of a restaurant, the AI may be trained, for example, to recognize if a requested food item is out of stock or no longer available, and items on the menu.

Data server 140 setup: A user stores basic electronic records on data server 140. For example, in the case of a restaurant, the electronic records may include a menu and in-stock items. In the case of a medical clinic, the Electronic Records may include an Electronic Medical Record (ERM) or Electronic Health Record (EHR).

Robot 120 Setup: The robot 120 may be initialized by a process similar to that disclosed in application Ser. No. 18/149,183 which was published as US 2023/0244230 on Aug. 3, 2023, the invention of which is incorporated herein by reference. Additionally, details listed in the exemplary cases below may be applied. Initially, any required applications or processes may be downloaded and installed on the robot.

Non-Limiting Examples of Use Cases of Embodiments of the Invention:

Medical Example:

In an embodiment of the invention, the system is used for a doctor to send over a medical report on a consultation to be stored in an EHR. Participants in this example can also be other medical staff practitioners. This example includes a doctor but may also include a nurse, physician's assistant, resident, etc. A patient has a consultation with a doctor. During the consultation, data may be generated that will need to be placed in an EHR system. Examples of gathering data include: Vitals, medical tests, blood tests, prescriptions, Doctor's notes and dictations, etc. Examples of the methods used to gather data include: dictation, speech to text (STT), Microphone, Camera, touch screen, screen, keyboard, mouse, directly by robot 120 or indirectly via a kiosk/computer/mobile device that communicates with the robot.

In an embodiment of the invention, the kiosk/robot/computer/mobile device adds tags to the report to identify the report. The tags in a simple example may be "medicine" and in a more complex example "prescription", "opioids", "25 mg/2x a day", and "30-year-old female", etc. to more accurately reflect the summary report 150.

The Doctor may additionally or alternatively have the option to manually select tags and/or confirm a pre-selected set of tags. The Doctor toward the end of the consultation or post-consultation will upload the new patient data. Once the tags have been added, the patient data may be uploaded at any point.

The uploaded report is received by robot 120 and forwarded to analysis server 130. Optionally, the robot may attach additional files/information related to participants of the consultation. Once received, the AI model may add additional tags to the report. The AI model may then use data or a subset of data of at least one of an EHR and a medical data library. The AI model uses the data to run validation checks on the report. The AI runs one or more validation checks on the reports until the report is satisfactory.

Examples of validation checks may include medicine interaction, medicine dosage, diagnostics accuracy, medicine side effects, etc. Optionally, the AI model then adds a tag to the report indicating pass or fail. In the case of a pass, the analysis server 130 will send the report to the EHR system to be stored as a medical record. A notification may be sent to all necessary recipients that a new report has been uploaded to the EHR. In the case of a fail, the AI model will send back the report (e.g., to the robot 120), optionally highlighting the information that resulted in a fail, or with an additional report that the AI model has written detailing the reason or reasons for failure. All recipients of the report may also receive a notification of the returned and altered report. The AI model may additionally provide suggested changes to correct the problems in the report 150. For example, reducing or increasing a dosage level to an appropriate range, providing alternative choices of prescription, etc. The analysis server 130 or the robot 120 may additionally send back the failure report to a supervisor of the doctor. The doctor receives the altered report possibly with suggested changes or fixes and reviews the altered report. The doctor will then either, accept the rejection and make the necessary changes, for example to accept the suggestions of the AI model, or reject the reasons for failure or rejects the suggestions made by the AI model.

If the doctor accepts the changes, the doctor will then upload the report back to the analysis server 130 (e.g., directly or via the robot). The process will then flow the same as when initially uploaded to the central server listed above.

If the doctor disagrees and rejects the suggestions, the doctor, if authorized, will upload the report 150 directly to the EHR and if not authorized may be able to send it to a higher authority or colleague to review the rejections.

At the end of the process, the EHR will receive and store a validated medical record.

Restaurant Example:

In an embodiment of the invention, system 100 is used for ordering food at a restaurant by a customer. The participant 110 is a customer ready to order food from the robot that serves as the waiter or the participant is a waiter or staff member taking down a customer's order with the help of the robot 120. Optionally, the participant/customer places an order for a hamburger via touch screen selection, dictation, typing, etc. to fill out the summary report 150 on the robot 120. The robot 120 adds tags to the report 150 to identify the report 150.

In an embodiment of the invention, in an example, the tags can be "food" and in a more complex example "food", "burger", "medium-rare", and "no pickles" to more accurately reflect the customer's order. Optionally, the customer can manually select tags and/or confirm a pre-selected set of tags. The robot 120 then forwards the report 150 to analysis server 130. The analysis server 130 activates the AI model 132 using its knowledge of food, food sanitation, menu items, etc. to analyze the report and flag any mistakes or warnings and return a pass or fail result. In the case of "pass", for example, the order is correct and is sent to the order list on data server 140. In the case of "fail", for example, that lettuce is out of stock, the analysis server 130 sends the "report" back to the robot 120, possibly with suggested revisions. In the case of lettuce being out of stock, the revision may be suggesting for the customer to replace the lettuce with arugula or confirming to receive a hamburger without lettuce.

The customer may accept or reject the suggested changes, and/or make new changes, and re-submit the order to the analysis server. Any subsequent order will be received by the analysis server 130 and processed by the AI model 132 as before.

In an embodiment of the invention, sending the order/report 150 between the robot 120 and analysis server 130 may occur in a loop until the order passes the AI model test. Alternatively, if the participant has administrative access, he or she may override the test and send the data straight to the data server 140, which in this case stores an order list. This may be the case if the participant inputting the order is a worker of the restaurant and not a customer. Optionally, the restaurant worker may know that the restaurant just received a new shipment of lettuce but the inventory has not been updated yet. Once the order is approved by the AI model 132 or once an administrator overrides the AI, the order is stored to be accessible for execution. The order is then received by the kitchen staff and the customer gets his burger.

In an embodiment of the invention, system 100 is controlled by software models that can be backed up on a non-transitory memory device, for example a DVD, USB disk, external disk or other devices and can be provided physically to a robot 120 and a server computer 130 for installation and execution.

It should be appreciated that the above-described methods and apparatus may be varied in many ways, including omitting or adding elements or steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

It will be appreciated by persons skilled in the art that the present invention is not limited to what has been particularly shown and described hereinabove. Rather the scope of the present invention is defined only by the claims, which follow.

What is claimed is:

1. An interacting computational robot system comprising:
an analysis server computer; and,
a robot configured to participate in interactions with at least one participant and collect information related to the at least one participant;
wherein the robot generates a summary report based on the collected information or accepts the summary report from the at least one participant;
wherein the robot is configured to transmit the summary report to the analysis server for analysis;
wherein the analysis server is configured to analyze the summary report and provide an indication of whether the summary report passes or fails based on predetermined criteria;
when the summary report is determined to pass, the summary report is stored in a database, and when the summary report is determined to fail, the analysis server generates feedback to the robot with a list of one or more corrections needed for the summary report, and
wherein the analysis server receives alterations and corrections provided by a user that has reviewed the generated feedback of the summary report.

2. The interacting computational robot system of claim 1, further comprising a display for communicating with the at least one participant.

3. The interacting computational robot system of claim 2, wherein the list of one or more corrections is provided to the at least one participant by way of the display, and the display is operable to receive further input from the at least one participant relating to the one or more corrections.

4. The interacting computational robot system of claim 2, further comprising a graphical user interface utilizing a selected set of data fields, wherein the analysis server computer is further configured to utilize one or more data tags corresponding to at least one of the data fields.

5. The interacting computational robot system of claim 4, wherein the data tags comprise hierarchical data tags.

6. The interacting computational robot system of claim 1, wherein the predetermined criteria are developed using a trained AI model, a large language AI model, or a convolutional neural network AI model.

7. The interacting computational robot system of claim 6, wherein at least one of the AI models is developed using information from the at least one participant or information from a database of different participants and is further configured to determine patterns between new participant information, background information, or the pass/fail determination of summary reports.

8. The interacting computational robot system of claim 1, wherein the robot further comprises one or more sensors to collect information from the at least one participant, the one or more sensors including a microphone, a camera, or an interface to receive vital sign information from the at least one participant.

9. The interacting computational robot system of claim 1, wherein the summary report relates to a medical status of the at least one participant and includes medication information, allergy information, or medical condition.

10. The interacting computational robot system of claim 1, wherein the summary report relates to a food order and includes information pertaining to food allergies, food availability, or food alternatives.

11. A method of utilizing an interacting computational robot system comprising the following steps:
providing an analysis server computer;
utilizing a robot configured to participate in interactions with at least one participant;
collecting, by the robot, information relating to the at least one participant;
generating a summary report by the robot based on the collected information or accepting the summary report from the at least one participant;
transmitting the summary report by the robot to the analysis server for analysis;
analyzing the summary report by the analysis server computer and providing an indication of whether the summary report passes or fails based on predetermined criteria;
when the summary report is determined to pass, the summary report is stored in a database, and when the summary report is determined to fail, the analysis server generates feedback to the robot with a list of one or more corrections needed for the summary report, and
wherein the analysis server receives alterations and corrections provided by a user that reviewed the generated feedback of the summary report.

12. The method of utilizing an interacting computational robot system of claim 11, further comprising utilizing a display for communicating with the at least one participant.

13. The method of utilizing an interacting computational robot system of claim 12, further comprising providing the list of one or more corrections to the at least one participant by way of the display, and the display is operable to receive further input from the at least one participant relating to the one or more corrections.

14. The method of utilizing an interacting computational robot system of claim 12, further comprising utilizing a graphical user interface having a selected set of data fields, wherein the analysis server computer is further configured to utilize one or more data tags corresponding to at least one of the data fields.

15. The method of utilizing an interacting computational robot system of claim 14, wherein the data tags comprise hierarchical data tags.

16. The method of utilizing an interacting computational robot system of claim 11, further comprising developing the predetermined criteria using a trained AI model, a large language AI model, or a convolutional neural network AI model.

17. The method of utilizing an interacting computational robot system of claim 16, further comprising developing at least one of the AI models using information from the at least one participant or information from a database of different participants and is further configured to determine patterns between new participant information, background information, or the pass/fail determination of summary reports.

18. The method of utilizing an interacting computational robot system of claim 11, further comprising using one or more sensors to collect information from the at least one participant, the one or more sensors including a microphone, a camera, or an interface to receive vital sign information from the at least one participant.

19. The method of utilizing an interacting computational robot system of claim 11, wherein the summary report relates to a medical status of the at least one participant and includes medication information, allergy information, or medical condition.

20. The method of utilizing an interacting computational robot system of claim 11, wherein the summary report relates to a food order and includes information pertaining to food allergies, food availability, or food alternatives.

21. A non-transitory computer readable storage medium comprising computer instructions that when executed by a processor cause the processor to execute the method of claim 11.

* * * * *